(12) United States Patent
Fujisawa et al.

(10) Patent No.: US 10,921,482 B2
(45) Date of Patent: Feb. 16, 2021

(54) MID-INFRARED CARBON DIOXIDE SENSOR

(71) Applicant: SCHLUMBERGER TECHNOLOGY CORPORATION, Sugar Land, TX (US)

(72) Inventors: Go Fujisawa, Sagamihara (JP); Sheng Chao, Cambridge (GB); Timothy Jones, Cambridge (GB); Nathan Lawrence, Cambridge (GB); Rolf Rustad, Rada (NO); Li Jiang, Sugar Land, TX (US); Steven Gahlings, Cambridgeshire (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/511,164

(22) PCT Filed: Sep. 9, 2015

(86) PCT No.: PCT/US2015/049058
§ 371 (c)(1),
(2) Date: Mar. 14, 2017

(87) PCT Pub. No.: WO2016/044005
PCT Pub. Date: Mar. 24, 2016

(65) Prior Publication Data
US 2017/0242149 A1    Aug. 24, 2017

(30) Foreign Application Priority Data

Sep. 15, 2014   (GB) .................................. 1416256

(51) Int. Cl.
*G01V 8/10* (2006.01)
*G01N 21/3504* (2014.01)
(Continued)

(52) U.S. Cl.
CPC ............... *G01V 8/10* (2013.01); *E21B 49/08* (2013.01); *G01N 21/3504* (2013.01);
(Continued)

(58) Field of Classification Search
CPC ........................................................ G01V 8/10
See application file for complete search history.

(56) References Cited

U.S. PATENT DOCUMENTS

| 4,922,714 A | 5/1990 | Grob et al. |
| 5,049,742 A | 9/1991 | Hosonuma et al. |

(Continued)

FOREIGN PATENT DOCUMENTS

| CN | 1321882 A | 11/2001 |
| CN | 101893558 A | 11/2010 |

(Continued)

OTHER PUBLICATIONS

Hawkins, G. et al., "Cooled infrared filters and dichroics for the sea and land surface temperature radiometer", Applied Optics, 2013, 52(10), pp. 2125-2135.
(Continued)

*Primary Examiner* — Edwin C Gunberg

(57) ABSTRACT

A sensor for monitoring $CO_2$ in a fluid regardless of the phase properties of the fluid, i.e., regardless of whether the fluid contacting the window is a liquid water-based phase, a liquid oil-based phase, a mixture of liquid water and liquid oil-based phases, or a gas phase. The sensor includes an internal reflection window for contacting with the fluid. A mid-infrared light source directs a beam of mid-infrared radiation into the window and the beam is internal reflected at an interface between the window and the fluid. The reflected beam is passed through three narrow bandpass filters which preferentially transmit mid-infrared radiation over bands of wavelengths corresponding to absorbance
(Continued)

peaks of water, oil and $CO_2$. The amount of $CO_2$ is determined from the intensities of the mid-infrared radiation passing through the three filters

18 Claims, 9 Drawing Sheets

(51) Int. Cl.
  *G01N 33/00*   (2006.01)
  *G01N 21/3577*  (2014.01)
  *G01N 21/552*   (2014.01)
  *E21B 49/08*   (2006.01)
  *G01N 21/15*   (2006.01)

(52) U.S. Cl.
  CPC ....... *G01N 21/3577* (2013.01); *G01N 21/552* (2013.01); *G01N 33/004* (2013.01); *E21B 49/0875* (2020.05); *G01N 21/15* (2013.01); *G01N 2021/152* (2013.01); *G01N 2021/154* (2013.01); *G01N 2201/068* (2013.01); *G01N 2201/0696* (2013.01); *G01N 2201/12* (2013.01); *Y02A 50/20* (2018.01)

(56) References Cited

U.S. PATENT DOCUMENTS

| | | |
|---|---|---|
| 5,621,166 A | 4/1997 | Butler |
| 5,859,430 A | 1/1999 | Mullins et al. |
| 6,147,762 A | 11/2000 | Haschberger et al. |
| 6,215,592 B1 | 4/2001 | Pelekhaty |
| 6,343,167 B1 | 1/2002 | Scalora et al. |
| 6,507,396 B1 | 1/2003 | Godfried et al. |
| 6,627,873 B2 | 9/2003 | Tchakarov et al. |
| 6,888,127 B2 | 5/2005 | Jones et al. |
| 6,958,818 B1 | 10/2005 | Payne |
| 6,995,360 B2 | 2/2006 | Jones et al. |
| 7,123,416 B1 | 10/2006 | Erdogan et al. |
| 7,407,566 B2 | 8/2008 | Jiang et al. |
| 7,697,141 B2 | 4/2010 | Jones et al. |
| 7,804,598 B2 | 9/2010 | Hall et al. |
| 9,013,702 B2 | 4/2015 | Freese |
| 2003/0062472 A1 | 4/2003 | Mullins et al. |
| 2003/0147159 A1 | 8/2003 | Dube et al. |
| 2005/0269499 A1 | 12/2005 | Jones et al. |
| 2006/0097203 A1 | 5/2006 | Bykanov et al. |
| 2006/0139646 A1 | 6/2006 | DiFoggio |
| 2006/0175547 A1 | 8/2006 | DiFoggio et al. |
| 2006/0177939 A1 | 8/2006 | Lehmann et al. |
| 2008/0165356 A1 | 7/2008 | DiFoggio et al. |
| 2008/0173805 A1 | 7/2008 | Indo et al. |
| 2010/0195105 A1 | 8/2010 | Myrick et al. |
| 2010/0206199 A1 | 8/2010 | Beuchle et al. |
| 2011/0228279 A1 | 9/2011 | Lucey |
| 2012/0025103 A1 | 2/2012 | Deshmukh et al. |
| 2012/0162380 A1 | 6/2012 | Cho et al. |
| 2012/0170023 A1 | 7/2012 | Szobota et al. |
| 2012/0290208 A1* | 11/2012 | Jiang .................. G01N 21/3504 702/8 |
| 2013/0056626 A1 | 3/2013 | Shen et al. |
| 2013/0070231 A1 | 3/2013 | Nauka et al. |
| 2013/0284900 A1 | 10/2013 | Freese et al. |
| 2014/0076551 A1 | 3/2014 | Pelletier et al. |
| 2015/0114631 A1 | 4/2015 | Chen et al. |
| 2016/0139296 A1 | 5/2016 | Perkins et al. |
| 2016/0231459 A1 | 8/2016 | Perkins et al. |
| 2017/0241899 A1 | 8/2017 | Jones et al. |
| 2017/0242150 A1 | 8/2017 | Jones et al. |
| 2018/0231684 A1 | 8/2018 | Jones et al. |
| 2020/0165916 A1 | 5/2020 | Jones et al. |

FOREIGN PATENT DOCUMENTS

| | | |
|---|---|---|
| CN | 102346138 A | 2/2012 |
| CN | 102854167 A | 1/2013 |
| CN | 103257122 A | 8/2013 |
| CN | 203658252 U | 6/2014 |
| CN | 104359852 A | 2/2015 |
| DE | 10255769 A1 | 6/2004 |
| DE | 102010045643 A1 | 3/2012 |
| EP | 0795744 A1 | 9/1997 |
| EP | 1967872 A1 | 9/2008 |
| GB | 2345753 A | 7/2000 |
| GB | 2395553 A | 5/2004 |
| GB | 2402476 A | 12/2004 |
| GB | 2507959 A | 5/2014 |
| JP | S5831307 A | 2/1983 |
| JP | 2013054368 A | 3/2013 |
| KR | 20120075182 A | 7/2012 |
| WO | WO0140771 A2 | 6/2001 |
| WO | WO2006063094 A1 | 6/2006 |
| WO | WO2009000490 A1 | 12/2008 |
| WO | WO2012073791 A1 | 6/2012 |
| WO | WO2016044008 A1 | 3/2016 |
| WO | WO2016048655 A1 | 3/2016 |

OTHER PUBLICATIONS

Baker, M. L. et al., "Effects of the Variation of Angle of Incidence and Temperature on Infrared Filter Characteristics", Applied Optics, 1967, 6(8), pp. 1343-1351.
Belyaeva, A. I., "Cryogenic infrared multilayer filters: the origin of low temperature shift in the pass-band edge", Proceedings of SPIE, 1999, 3890, pp. 87-92.
Blifford, I. H., "Factors Affecting the Performance of Commercial Interference Filters", Applied Optics, 1966, 5(1), pp. 105-111.
Born, M. et al., "Principles of Optics", pp. 323-333, 6th edition, Pergamon Press, Oxford (1980).
Chen, T-C. et al., "Influences of Temperature and Stress on Transmission Characteristics of Multilayer Thin-Film Narrow Bandpass Filters", Japanese Journal of Applied Physics, Part 1, 40(6A), pp. 4087-4096.
Evans, C. S. et al., "Filters for v2 band of CO2: monitoring and control of layer deposition", Applied Optics, 1976, 15(11), pp. 2736-2745.
Harrick, N. J., "Internal Reflection Spectroscopy", Wiley Interscience, New York, New York, USA, 1967, pp. 43-44.
Heath, D. F., et al., "Characterization of a "hardened" ultrastable UV linear variable filter and recent results on the radiometric stability of narrow band interference filters subjected to temperature/humidity, thermal/vacuum and ionizing radiation environments", SPIE, 1998, 3501, pp. 401-411.
Kaplan, S. G. et al., "Characterization of narrowband infrared interference filters", Proceeding of SPIE, 1998, 3425, 48-55.
Kim, S-H. et al., "Temperature Dependence of Transmission Center Wavelength of Narrow Bandpass Filters Prepared by Plasma Ion-Assisted Deposition", Journal of Korean Physical Society, 2004, 45(1), pp. 93-98.
Li, B. et al., "Improving low-temperature performance of infrared thin-film interference filters utilizing the intrinsic properties of IV-VI narrow-gap semiconductors", Optics Express, 2004, 12(3), pp. 401-404.
Li, B. et al., "Recent progress in improving low-temperature stability of infrared thin-film interference filters", Optics Express, 2005, 13(17), pp. 6376-6380.
MacLeod, H. A., "Production Methods and Thin-Film Materials" in Thin-Film Optical Filters, 4th edition, pp. 489-568, CRC Press, Boca Raton, Florida (2010).
Mansuno, K. et al., "Enhanced Contrast of Wavelength-Selective Mid-Infrared Detectors Stable Against Incident Angle and Temperature Changes", Japanese Journal of Applied Physics, 2011, 50(3R), p. 037201 (7 pages).
Piccioli, N. et al., "Optical Constants and Band Gap of PbTe from Thin Film Studies Between 25 and 300 K", Journal of Physics Chemical Solids, 1974, 35, pp. 971-977.
Ritter, E. et al., "Influence of Substrate Temperature on the Condensation of Vacuum Evaporated Films of MgF2 and ZnS", Journal of Vacuum Science and Technology, 1969, 6, pp. 733-736.

(56) References Cited

OTHER PUBLICATIONS

Sakaguchi, S., "Temperature Dependence of Transmission Characteristics of Multilayer Film Narrow Bandpass Filters", Japanese Journal of Applied Physics, 1999, 38, pp. 6362-6368.
Seeley, J. S. et al., "Temperature-invariant and other narrow-band IR filters containing PbTe, 4-20 [micrometers]", Proceedings of the Society of Photo-Optical Instrumentation Engineers, 1980, 246, pp. 83-94.
Takahashi, H., "Temperature stability of thin-film narrow-bandpass filters produced by ion-assisted deposition", Applied Optics, 1995, 34(4), pp. 667-675.
Thelen, A., "Multilayer Filters with Wide Transmittance Bands", Journal of the Optical Society of America, 1963, 53(11), pp. 1266-1279.
Tsai, R-Y., et al., "Thermally stable narrow-bandpass filter prepared by reactive ion-assisted sputtering", Applied Optics, 2001, 40(10), pp. 1593-1598.
Weiting, F. et al., "Temperature Effects on the Refractive Index of Lead Telluride and Zinc Selenide", Infrared Physics, 1990, 30(4), pp. 371-373.
Wiechmann, S. et al., "Thermo-optic properties of $TiO_2$, $Ta_2O_5$ and $Al_2O_3$ thin films for integrated optics on silicon", Thin Solid Films, 2009 517(24), pp. 6847-6849.
Zemel, J. N. et al., "Electrical and Optical Properties of Epitaxial Films of PbS PbSe PbTe and SnTe", Shys. Rev, 1965, 140, pp. A330-A343.
Roithner LaserTechnik GmbH Mid-IR Products Brochure, Sep. 2010, 4 pages.
Combined Search and Exam Report under Sections 17 and 18(3) in corresponding United Kingdom patent application No. 1416268.9 dated Jan. 29, 2015, 9 pages.
Exam Report under Section 18(3) in corresponding United Kingdom patent application No. 1416268.9 dated Aug. 29, 2017, 5 pages.
Search Report and Written Opinion of International Patent Application No. PCT/US2015/049094 dated Dec. 1, 2015, 13 pages.
Office Action issued in related U.S. Appl. No. 15/511,491 dated Sep. 18, 2018, 10 pages.
Combined Search and Exam Report under Sections 17 and 18(3) in corresponding United Kingdom patent application No. 1416256.4 dated Mar. 16, 2015, 6 pages.
Combined Search and Exam Report under Sections 17 and 18(3) in corresponding United Kingdom patent application No. 1416257.2 dated Jan. 14, 2015, 6 pages.
Search Report and Written Opinion of International Patent Application No. PCT/US2015/049065, dated Nov. 24, 2015, 18 pages.
Combined Search and Exam Report under Sections 17 and 18(3) in corresponding United Kingdom patent application No. 1416260.6 dated Jan. 26, 2015, 5 pages.
Search Report and Written Opinion of International Patent Application No. PCT/US2015/049554, dated Dec. 23, 2015, 8 pages.
Office Action issued in related U.S. Appl. No. 15/511,343 dated Feb. 21, 2018, 26 pages.
Combined Search and Exam Report under Sections 17 and 18(3) in corresponding United Kingdom patent application No. 1416264.8 dated Mar. 16, 2015, 6 pages.
Search Report and Written Opinion of International Patent Application No. PCT/US2015/049086 dated Dec. 21, 2015, 15 pages.
Office Action issued in related U.S. Appl. No. 15/511,336 dated Jun. 18, 2018, 14 pages.
Combined Search and Exam Report under Sections 17 and 18(3) in corresponding United Kingdom patent application No. 1416265.5 dated Mar. 12, 2015, 8 pages.
Exam Report under Section 18(3) in corresponding United Kingdom patent application No. 1416265.5 dated Oct. 4, 2016, 3 pages.
Search Report and Written Opinion of International Patent Application No. PCT/US2015/049061 (IS14.9034-Wo-PCT), dated Dec. 23, 2015, 17 pages.

Final Office Action issued in related U.S. Appl. No. 15/511,343 dated Oct. 5, 2018, 25 pages.
CSI Technologies, Analytical Testing and Analysis: Support for Drilling and Completions Fluids Technology, available at https://web.archive.org/web/20140929045212/http://csi-tech.net/assets/literature/analytical-testing-and-analysis.pdf,Sep. 24, 2014, 2 pages.
Tropf et al, Optical materials: visible and infrared, Chapter 11 of Electro-Optics Handbook, R.W. Waynant and M.N. Ediger, eds., Second edition, McGraw-Hill, New York, 2000, 125 pages.
Boston Electronics Corporation, IR Sources, Jul. 2004, 16 pages.
Office Action in Chinese Patent Application No. 201580061274.4, dated Jan. 29, 2019, 4 pages.
Office Action in U.S. Appl. No. 15/511,333, dated Jan. 10, 2019, 19 pages.
Office Action in U.S. Appl. No. 15/511,343, dated Mar. 4, 2019, 39 pages.
First Office Action and Search Report issued in related Chinese Patent Application No. 201580061273.X dated Mar. 11, 2019, English Translation, 12 pages.
Kong, C. et al., "Separation and Structural Identification of Organics", Beijing Chemical Industry Press, 1st Edition, 13 pages.
Fernandez-Carrasco et al., "Infrared spectroscopy in the analysis of building and construction materials" Theophile, Ed., Infrared Spectroscopy—Materials Science, Engineering and Technology (InTech), 2012, pp. 369-382.
Giguere, et al., "On the infrared absorption of water and heavy water in condensed states", Canadian Journal of Chemistry, 1956, 34(6), pp. 798-808.
Thermal Measurement and Automatic Adjustment (Intermediate Level), the Ministry of Machinery Industry of the People's Republic of China, the technical training material for mechanical workers, eds: FENG Jiping et al., Beijing, Popular Science Press, 1987, pp. 429-431.
Whateley, "Carbonate species and not polywater formed on Magnesium Oxide", Nature Physical Science, 1971, 231, pp. 178-179.
Exam Report under Section 18(3) in UK Patent Application No. 1416268.9, dated Aug. 1, 2018, 3 pages.
Search Report and Written Opinion of International Patent Application No. PCT/US2015/049094, dated Dec. 17, 2015, 13 pages.
International Preliminary Report on Patentability of International Patent Application No. PCT/US2015/049094, dated Mar. 30, 2017, 10 pages.
Second Office Action and Search Report issued in Chinese Patent Application No. 201580061273.X, dated Nov. 12, 2019, 10 pages.
Office Action issued in U.S. Appl. No. 16/695,671, dated Mar. 19, 2020, 7 pages.
Second Office Action in Chinese Patent Application No. 201580061274.4, dated Aug. 21, 2019.
Office Action and Search Report issued in Norwegian Patent Application No. 20170480, dated Jan. 23, 2020, 5 pages.
Office Action issued in U.S. Appl. No. 15/511,343, dated Jun. 20, 2019, 27 pages.
Office Action issued in U.S. Appl. No. 15/511,343, dated Sep. 5, 2019, 32 pages.
Office Action issued in U.S. Appl. No. 15/511,343, dated May 6, 2020, 34 pages.
Exam Report under Section 18(3) in UK Patent Application No. 1416265.5, dated Mar. 2, 2017, 3 pages.
Office Action in Norwegian Patent Application No. 20170393, dated Jan. 23, 2020, 4 pages.
Notice of Allowance issued in U.S. Appl. No. 15/511,437, dated Nov. 15, 2018, 9 pages.
Taylor, H. F. W., "Cement Chemistry", Academic Press, London, 1990, pp. 199-242.
Sullivan, B.T. et al, "Implementation of a numerical needle method for thin-film design," Applied Optics, vol. 35, 1996, pp. 5484-5492.
Dobrowolski, J.A. et al., "Refinement of optical multilayer systems with different optimization procedures", Applied optics, vol. 29, 1990, pp. 2876-2893.

* cited by examiner

MID-INFRARED CARBON DIOXIDE SENSOR

BACKGROUND

Embodiments of the present disclosure relate to mid-infrared sensing, and more particularly but not by way of limitation to a mid-infrared sensor for monitoring carbon dioxide ($CO_2$) in a fluid.

The analysis of chemical composition of fluid samples from hydrocarbon wells for the determination of phase behaviour and chemical composition is a critical step in the monitoring and management of a hydrocarbon well as well as the evaluation of the producibility and economic value of the hydrocarbon reserves. Similarly, the monitoring of fluid composition during production or other operations can have an important bearing on reservoir management decisions. Similarly, determination of phase behaviour and chemical composition is important in pipelines and the like used to convey/transport hydrocarbons from the wellhead, including subsea pipelines.

Several disclosures have described analysis of specific gases in borehole fluids in the downhole environment using near-infrared (e.g. $\lambda$=1-2.5 μm) spectral measurements. For example, U.S. Pat. No. 5,859,430 describes the use of near-infrared spectroscopy to determine quantitatively the presence of methane, ethane and other simple hydrocarbons in the gas phase. The gases were detected using the absorption of near-infrared radiation by the overtone/combination vibrational modes of the molecules in the spectral region 1.64-1.75 μm.

More recently, U.S. Pat. No. 6,995,360 describes the use of mid-infrared radiation with a wavelength $\lambda$=3-5 μm to monitor gases in downhole environments, and U.S. Patent Publication No. 2012/0290208 proposes the use of mid-infrared radiation to monitor sequestered carbon dioxide dissolved into the liquid solutions of saline aquifers.

There are however many technical problems with using mid-infrared sensors in the hydrocarbon industry and processing information from such sensors. Additionally, much of the utility of mid-infrared spectroscopy for $CO_2$ monitoring has not previously been recognized.

SUMMARY

Accordingly, in a first aspect, in accordance with an embodiment of the present disclosure, a sensor for monitoring $CO_2$ in a fluid is provided, where the sensor includes:
- an internal reflection window for contacting with the fluid;
- a mid-infrared radiation source for directing a beam of mid-infrared radiation into said window, where the beam undergoes attenuated internal reflection at an interface between the window and the fluid;
- a set of three first-narrow-bandpass filters, where the narrow bandpass filters are each configured to preferentially transmit mid-infrared radiation over bands of wavelengths corresponding to respective absorbance peaks of water, oil and $CO_2$ to filter the internally reflected mid-infrared radiation received from the window;
- one or more infrared detectors for detecting the filtered mid-infrared radiation that is transmitted through the set of filters; and
- a processor that is configured to process/measures the intensities of the detected mid-infrared radiation transmitted through the set of filters, and determine therefrom an amount (e.g. a concentration) of $CO_2$ in the fluid.

By using a set of three filters in the first aspect, the sensor can measure the $CO_2$ whether the fluid contacting the window is a liquid water-based phase, a liquid oil-based phase, a mixture of liquid water and liquid oil-based phases, or a gas phase.

Such a sensor is highly flexible as it is not necessary for a determination of $CO_2$ concentration that the window is in contact with a liquid, i.e. it can be in contact with a liquid or a gas. In general, attenuated total reflection mid-infrared sensing can only be used to sense condensed phases, but a sensor in accordance with an embodiment of the present disclosure may measure $CO_2$ in uncondensed phases, because the $CO_2$ is strongly absorbing in the mid-infrared at a wavelength of about 4.3 μm.

As discussed below, the sensor may be part of a sensor arrangement e.g. with a further similar sensor for obtaining a reference intensity.

In a second aspect, in accordance with an embodiment of the present disclosure, the use of the sensor, or sensor arrangement, of the first aspect is provided to determine an amount (e.g. a concentration) of $CO_2$ in a fluid. Thus, a method of monitoring $CO_2$ in a fluid may include: providing the sensor of the first aspect such that the internal reflection window is in direct contact with the fluid; and operating the sensor to determine an amount (e.g. a concentration) of $CO_2$ in the fluid.

In a third aspect, in accordance with an embodiment of the present disclosure, a well tool is provided (such as a drilling, production well or wireline sampling tool) including the sensor, or sensor arrangement, of the first aspect.

Optional features of embodiments of the present disclosure will now be set out. These are applicable singly or in any combination with any aspect of the embodiments of the present disclosure.

In accordance with an embodiment of the present disclosure, the transmission band of the first filters may be located at about 3330 cm$^{-1}$ (water), 2900 cm$^{-1}$ (oil) and 2340 cm$^{-1}$ ($CO_2$).

In accordance with an embodiment of the present disclosure, the fluid may be a production fluid, drilling fluid, completion fluid or a servicing fluid. The fluid may in some embodiments comprise a liquid/gas mixture.

"Mid-infrared radiation," as used herein means that the radiation has a wavelength in the range from about 2 to 20 μm. In some embodiments, mid-infrared radiation be in the range from about 3 to 12 μm or from 3 to 10 μm.

In some embodiments of the present disclosure, each first narrow bandpass filter may be configured such that its wavelength transmission band is substantially temperature invariant over temperatures in the range from about 25 to 150° C. Temperatures in downhole environments can vary greatly, e.g. from room temperature up to about 150° C. or 200° C. By using such a temperature invariant filter, the sensitivity of the sensor to shifts in temperature of its surroundings can be greatly reduced, providing for detection of $CO_2$ in the downhole environment and/or accurate measurement of the amount of $CO_2$.

To cover a greater range of downhole temperatures, the wavelength transmission band of the each first narrow bandpass filter may be substantially temperature invariant over all temperatures in the range from about 25 to 200° C. To cover both downhole and subsea conditions (where ambient temperatures can be in the range from about −25 to 25° C.), the wavelength transmission band of each first narrow bandpass filter may be substantially temperature invariant over all temperatures in the range from about −25 to 150 or 200° C.

"Substantially temperature invariant" as used herein means that the variance is at most about 0.1 nm/° C. In some embodiments of the present disclosure, the temperature invariance may be at most about 0.05, 0.03, 0.02 or 0.01 nm/° C.

In embodiments of the present disclosure, each filter may comprise an interference filter. Merely by way of example, in some embodiments of the present disclosure, each filter may include a substrate, formed of Si, $SiO_2$, $Al_2O_3$, Ge or ZnSe and/or the like, and at each opposing side of the substrate alternating high and low refractive index layers may be formed. In some embodiments of the present disclosure, the high refractive index layers can be formed of PbTe, PbSe or PbS and the low refractive index layers can be formed of ZnS, ZnSe and/or the like.

In embodiments of the present disclosure, each filter may have three or more half wavelength cavities. Many conventional filters display unacceptably high band shifts with increasing temperature. For example, shifts in the range 0.2 to 0.6 nm/° C. are typical. Transmissivities also tend to reduce with increasing temperature. These properties, have prevented/limited development of mid-infrared sensors. However, in accordance with embodiments of the present disclosure, by using a PbTe-based, a PbSe-based, a PbS-based interference filter and/or the like it is possible to substantially reduce band shifts and transmissivity reductions. For example, a PbTe-based interference filter, in accordance with an embodiment of the present disclosure, may have a band shift of only about 0.03 nm/° C. or less. As an alternative to PbTe, PbSe, PbS or the like, the high refractive index layers can be formed, in some embodiments of the present disclosure, of Ge or the like.

In some embodiments of the present disclosure, a reference intensity may be used in the determination of the amount of the $CO_2$ in the fluid. Thus, a sensor arrangement, in accordance with an embodiment of the present disclosure, may include the sensor of the first aspect and a further similar sensor which can be used to obtain this reference intensity. The further sensor can have similar features as the first sensor except that its narrow bandpass filter transmits mid-infrared radiation over a band of wavelengths corresponding to a reference portion of the absorbance spectrum of the fluid. In such a scenario, the processor arrangement can be a shared processor arrangement of both sensors.

Another option, however, is to obtain the reference intensity using the first sensor. For example, the sensor, in accordance with an embodiment of the present disclosure, may further include a second narrow bandpass filter configured to transmit mid-infrared radiation over a band of wavelengths corresponding to a reference portion of the absorbance spectrum of the fluid. In such embodiments, the or a further infrared detector may be used to detect filtered mid-infrared radiation transmitted through the second filter, and the processor arrangement may measure the reference intensity of the detected mid-infrared radiation transmitted through the second filter and use the measured reference intensity in the determination of the amount of the $CO_2$ in the fluid.

In some embodiments of the present disclosure, the first and second filters may be selectably positionable between a single detector and the window, or each of the first and second filters can have a respective detector. The second narrow bandpass filter may be configured such that its wavelength transmission band is substantially temperature invariant over all temperatures in the range from about 25 to 150° C. Other optional features of the first narrow bandpass filters pertain also to the second narrow bandpass filter. The transmission band of the second filter may be located at about 2500 $cm^{-1}$.

In some embodiments of the present disclosure, the beam of mid-infrared radiation may be pulsed. This can be achieved, for example, in some embodiments of the present disclosure, by providing a mechanical chopper between the source and the window, or by pulsing the source.

In some embodiments of the present disclosure, the source may be a broad band thermal source or a narrower band source such as a light emitting diode or a laser.

In some embodiments of the present disclosure, the detector may be a thermopile, a pyroelectric or (particularly in subsea applications, where the low ambient temperatures can provide cooling) a photodiode detector.

In some embodiments of the present disclosure, the window may comprise a diamond window or a sapphire window. In some embodiments of the present disclosure, the diamond windows can be formed by chemical vapour deposition. Sapphire has a cut off for mid-infrared radiation at wavelengths of about 5 to 6 microns, but sapphire windows can generally be formed more cheaply than diamond windows. Thus, for absorption peaks below the cut off (such as the $CO_2$ absorption peak at about 4.3 microns), sapphire may be a useful alternative to diamond. In particular, for a given cost a larger window can be formed.

In some embodiments of the present disclosure, the sensor may further include a heater which is operable to locally heat the window, thereby cleaning the surface of the window in contact with the fluid. For example, in some embodiments of the present disclosure, if the window includes a conductive or semiconductive material (e.g. an area of semiconductive boron-doped diamond), the heater can con comprise an electrical power supply which sends a current through the window to induce resistive heating thereof. For example, in some embodiments of the present disclosure, a diamond window can have a central mid-infrared transmissive (e.g. undoped) area and an encircling area of semiconductive boron-doped diamond. The heater can induce resistive heating of the encircling area, and the central area can then be heated by conduction of heat from the encircling area. In some embodiments of the present disclosure, the heater may heats the window to a peak temperature of at least 400° C. In some embodiments of the present disclosure, the heater may maintain a peak temperature for less than one microsecond.

Alternatively or additionally, in some embodiments of the present disclosure, the sensor may further include an ultrasonic cleaner which is operable to ultrasonically clean the surface of the window in contact with the fluid. As another option, the sensor may be provided with a pressure pulse arrangement which is operable to produce a pressure pulse in the fluid at the window, thereby cleaning the surface of the window in contact with the fluid. In some embodiments of the present disclosure, the arrangement may produce a pressure pulse of at least about 1000 psi (6.9 MPa) in the fluid.

In some embodiments of the present disclosure, the sensor may be located downhole.

To determine the amount of $CO_2$ in the fluid, in some embodiments of the present disclosure, the processor arrangement may calculate from the measured intensities of the mid-infrared radiation transmitted through the water and oil first filters the phase of the fluid, and may then calculate from the phase of the fluid and the measured intensity of the mid-infrared radiation transmitted through the $CO_2$ first filter the amount of $CO_2$ in the fluid. More particularly, in some embodiments of the present disclosure, the processor arrangement may use the refractive index of the fluid, derived from the phase of the fluid, in the calculation of the amount of $CO_2$ in the fluid.

Indeed more generally, in a fourth aspect, in accordance with an embodiment of the present disclosure, a method of determining an amount of $CO_2$ in a fluid is provided, including:

receiving respective measured intensities of mid-infrared radiation filtered by three narrow bandpass filters that are configured to preferentially transmit mid-infrared radiation over bands of wavelengths corresponding to respective absorbance peaks of water, oil and $CO_2$, where the mid-infrared radiation, prior to filtering, is produced by directing a beam of mid-infrared radiation into an internal reflection window for attenuated internal reflection at an interface between the window and a fluid in direct contact with the window;

calculating from the measured intensities of the mid-infrared radiation filtered by the water and oil filters the phase of the fluid, and calculating from the phase of the fluid and the measured intensity of the mid-infrared filtered by the $CO_2$ filter the amount of $CO_2$ in the fluid.

The method may further include: deriving the refractive index of the fluid from the calculated phase of the fluid. The refractive index can then be used in the calculation of the amount of $CO_2$ in the fluid.

Further aspects of embodiments of the present disclosure provide: a computer program comprising code which, when run on a computer, causes the computer to perform the method of the fourth aspect; a computer readable medium storing a computer program comprising code which, when run on a computer, causes the computer to perform the method of the fourth aspect; and a computer system programmed to perform the method of the fourth aspect.

BRIEF DESCRIPTION OF THE DRAWINGS

Embodiments of the invention will now be described by way of example with reference to the accompanying drawings in which.

Figure 1A:
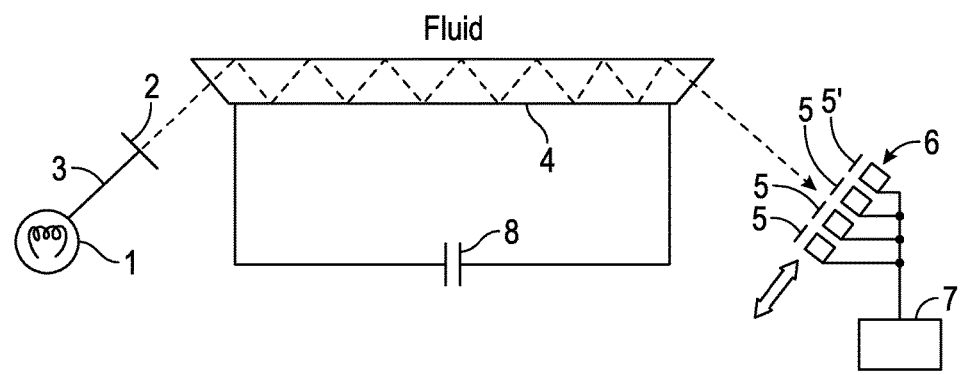
FIG. 1 shows schematically, in accordance with embodiments of the present disclosure: (a) a mid-infrared sensor, and (b) the sensor implemented as a module in a toolstring.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiment(s) only, and is not intended to limit the scope, applicability or configuration of the invention. Rather, the ensuing description of the preferred exemplary embodiment(s) will provide those skilled in the art with an enabling description for implementing a preferred exemplary embodiment of the invention, it being understood that various changes may be made in the function and arrangement of elements without departing from the scope of the invention.

Specific details are given in the following description to provide a thorough understanding of the embodiments. However, it will be understood by one of ordinary skill in the art that embodiments maybe practiced without these specific details. For example, well-known circuits, processes, algorithms, structures, and techniques may be shown without unnecessary detail in order to avoid obscuring the embodiments.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1(a) shows schematically a mid-infrared sensor, in accordance with an embodiment of the present disclosure, having a thermal broad band mid-infrared source 1, a mechanical chopper 2 that pulses a beam 3 of mid-infrared radiation which issues from the source, a diamond window 4, a set of selectively movable first narrow bandpass filters 5 and a second narrow bandpass filter 5', respective mid-infrared detectors 6 for the filters, and a processor arrangement 7. In some embodiments, the sensor may be encased in a protective housing allowing the sensor to be deployed downhole, the window 4 being positioned for contact with the fluid to be monitored. Mid-infrared waveguides (not shown) optically connect the source, window and the detectors. Suitable waveguides can be formed from optical fibres (e.g. hollow fibres or chalcogenide fibres), solid light pipes (e.g. sapphire pipes), or hollow light pipes (e.g. air or vacuum filled) with a reflective (e.g. gold) coating.

As the detector 6 changes its output with its temperature, even small changes in temperature can cause a large drift in signal output. However, in accordance with an embodiment of the present disclosure, pulsing the beam 3 allows the output signal of the detector to be frequency modulated, enabling removal of the environmental temperature effects from the signal. More particularly, the environment effects can be largely removed electronically by a high pass filter, because the time constant for environment effects tends to be much longer than the signal frequency. In some embodiments of the present disclosure, the detector output is AC-coupled to an amplifier. The desired signal can then be extracted e.g. electronically by lock-in amplification or computationally by Fourier transformation.

Instead of the thermal source 1 and the mechanical chopper 2, in some embodiments of the present disclosure, the pulsed beam 3 may be produced e.g. by a pulsable thermal source, light emitting diode or laser source. Pulsing the source in this way can give the same benefit of frequency modulation measurement, plus it can reduce resistive heating effects.

The beam 3 enters at one edge of the window 4, and undergoes a number of total internal reflections before emerging from the opposite edge. The total internal reflection of the infrared radiation at the fluid side of the window is accompanied by the propagation of an evanescent wave into the fluid. As the fluid preferentially absorbs certain wavelengths, depending on its chemical composition, this causes the emerging beam to have a characteristic variation in intensity with wavelength.

In some embodiments of the present disclosure, the window 4 is mechanically able to withstand the high pressures and temperatures typically encountered downhole. It is chemically stable to fluids encountered downhole and is transparent in the mid-IR wavelength region. In some embodiments of the present disclosure, the window may comprise diamond, sapphire and/or the like.

In accordance with an embodiment of the present disclosure, the first narrow bandpass filters 5 each transmit mid-infrared radiation over a band of wavelengths corresponding to an absorbance peak of a respective species in the fluid, while the second narrow bandpass filter 5' transmits mid-infrared radiation over a band of wavelengths corresponding to a reference portion of the absorbance spectrum of the fluid. The beam 3 then passes through a selected one of the narrow bandpass filters and is detected at the respective detector 6. Instead of having a plurality of detectors, each movable with its corresponding filter (as indicated by the double-headed arrow), in some embodiments of the present disclosure, a single detector is provided in front of which the filters are selectively movable.

In some embodiments of the present disclosure, the detector 6 may comprise, semiconductor photo-diodes (particularly in subsea applications), thermopiles or pyroelectric detectors.

The processor arrangement 7 receives a signal from the respective detector 6, which it processes to measure the intensity of the detected mid-infrared radiation transmitted through each filter 5, 5', and, as discussed in more detail below, determines therefrom an amount of the respective species in the fluid.

Also discussed in more detail below, the sensor may have a heater 8 which is operable to locally heat the window 4, thereby cleaning the surface of the window in contact with the fluid. Other options, however, are to clean the window ultrasonically (as described for example in U.S. Pat. No. 7,804,598), or with a mechanical wiper.

Figure 1B:
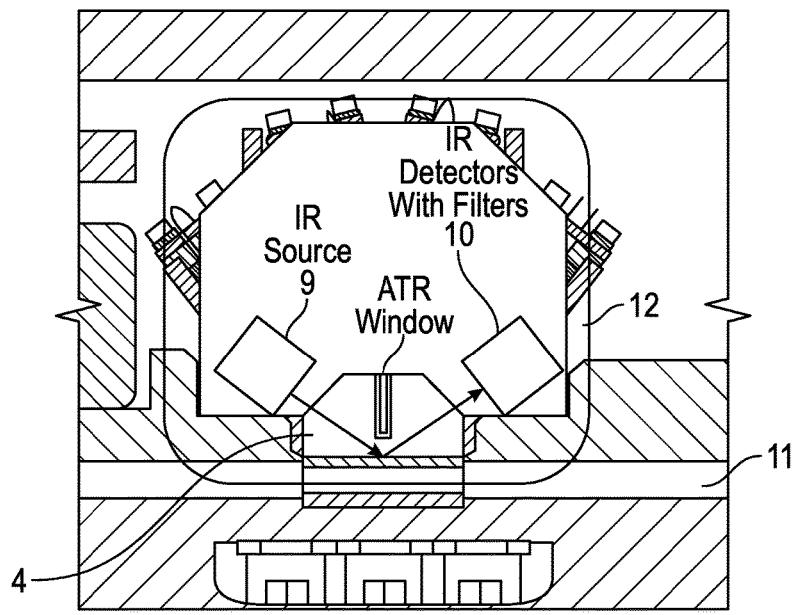

FIG. 1(b) shows schematically how, in accordance with an embodiment of the present disclosure, the sensor can be implemented as a module in a toolstring. In some embodiments of the present disclosure, the source 1 and chopper 2 are contained in a source unit 9 and filters 5, 5' and detectors 6 are contained in a detector unit 10. These may be located close to the window 4 that is in contact with a tool flowline 11. The sensor may be packaged in a protective metal chassis 12 to withstand the high pressure of the fluid in the flowline.

The window may be sealed into the chassis also to withstand the high pressures, and its packaging ensures no direct source light strays into the detectors.

Narrow Bandpass Filters

Figure 2:
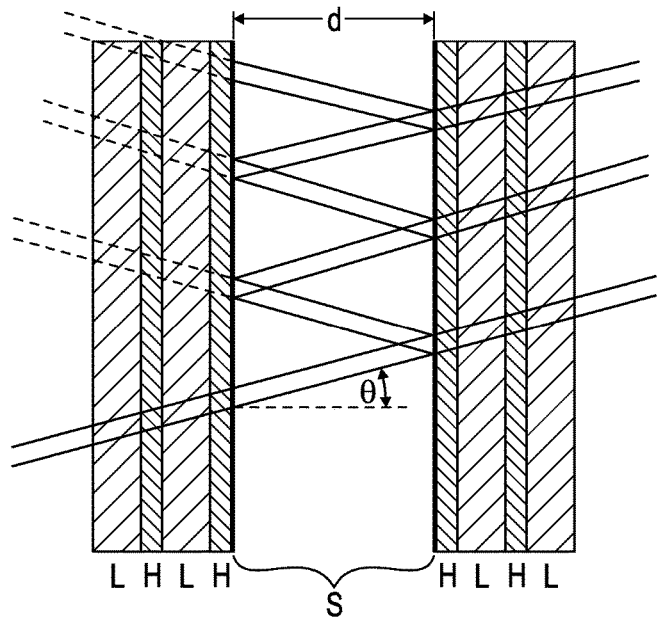
FIG. 2 shows schematically a narrow bandpass filter based on Fabry-Perot interferometry, in accordance with an embodiment of the present disclosure.

In embodiments of the present disclosure, the narrow bandpass filters 5, 5' may be based on Fabry-Perot interferometry. As shown in FIG. 2, each filter may have a substrate S of low refractive index and thickness d. On opposing surfaces of the substrate are stacked alternating high-reflectivity dielectric layers of high H and low L refractive index deposited onto the substrate using techniques such as ion-beam sputtering or radical-assisted sputtering. In some embodiments of the present disclosure, each layer in the stacks of alternating layers of high H and low L refractive index has an optical thickness of a quarter wavelength.

The optical thickness nd cos θ of the substrate S, where n is the refractive index of the substrate, is equal to an integer number of half wavelengths $\lambda_m$, where $\lambda_m$ is the peak transmission wavelength, corresponding approximately to the centre wavelength of the pass band of the filter. The condition for the transmission of radiation of wavelength $\lambda_m$ through the filter is thus $m\lambda_m/2 = nd \cos\theta$, where m is an integer.

The spectral region of conventional narrow bandpass dielectric filters designed to operate in the mid-infrared spectral regions shifts systematically to longer wavelengths with increasing temperature. The origin of the change in $\lambda_m$ with temperature is a change in the material properties with temperature of the dielectric materials that comprise the layers of the filter.

However, an approach described below, in accordance with an embodiment of the present disclosure, provides for the configuration and fabrication of mid-infrared narrow bandpass filters that have substantially temperature invariant optical properties over a wide temperature range.

The approach can be considered by the design of the filter:

$$(LH)^{x1}(LL)^{y1}(HL)^{x2}(LL)^{y2} \ldots (LL)^{yN}(HL)^{xN+1}$$

consisting of a total of y half wavelength spacers (cavities) LL of low refractive index material in N cycles ($y = \Sigma y_i$), LH being the stacks of $x_i$ quarter wavelength layers of alternating of high and low refractive index material in the N cycles. The reflections wavelength of the quarter wavelength reflector stack (which is the only reflection to undergo constructive interference), irrespective of the values of $x_i$ and N, can be expressed as:

$$\lambda_m = 2(n_L d_L + n_H d_H)$$

for first order reflections (m=0). The temperature variation of the wavelength in the reflector stack $d\lambda_m/dT|_s$, can be expressed as:

$$\frac{d\lambda_m}{dT}\bigg|_s = 2n_L d_L \left(C_L + \frac{dn_L}{n_L dT}\right) + 2n_H d_H \left(C_H + \frac{dn_H}{n_H dT}\right)$$

where $C_L$ and $C_H$ are the coefficients of linear expansion of the low and high refractive index materials, respectively. From eqn.[1] for first order reflection and normal incidence (i.e., m=1 and θ=0°), the corresponding temperature dependence $d\lambda_m/dT|_c$ of the cavity layer of low refractive index material is given by:

$$\frac{d\lambda_m}{dT}\bigg|_c = 2yn_L d_L \left(C_L + \frac{dn_L}{n_L dT}\right)$$

noting that y is the total number of half wavelength cavity layers. The total change in wavelength with temperature $d\lambda_m/dT|_T$ is given by the sum of $d\lambda_m/dT|_c$ and $d\lambda_m/dT|_s$:

$$\frac{d\lambda_m}{dT}\bigg|_T = 2(1+y)n_L d_L \left(C_L + \frac{dn_L}{n_L dT}\right) + 2n_H d_H \left(C_H + \frac{dn_H}{n_H dT}\right)$$

or $$\frac{d\lambda_m}{\lambda_m dT}\bigg|_T = (1+y)\left(C_L + \frac{dn_L}{n_L dT}\right) + \left(C_H + \frac{dn_H}{n_H dT}\right)$$

noting that $n_L d_L = n_H d_H$ at the temperature for which the filter is designed for use. Clearly $d\kappa_m/dT|_T$ can only be zero if the value of dn/dT for one of the materials is negative. This condition can be fulfilled by high refractive index materials such as PbTe, PbSe or PbS. For close matching of the value of $d\kappa_m/dT|_T$ to zero, the wavelength dependence of $n_i$ temperature and wavelength dependence of $dn_i/dT$ can be taken into account.

The condition $d\kappa_m/dT|_T = 0$ is given approximately by:

$$\frac{dn_H}{n_H dT} = -(1+y)\frac{dn_L}{n_L dT}$$

noting that $C_i$ is considerably smaller than $dn_i/n_i dT$ for most materials used in mid-infrared filters. The term (1+y) can be chosen to satisfy the above expression depending on the choice of low refractive index material. For example, with ZnSe and PbTe for the low and high refractive index materials, respectively, and using the material values of bulk phases $n_L=2.43$, $n_H=6.10$, $dn_L/dT=6.3\times10^{-5}$ K$^{-1}$ and $dn_H/dT=-2.1\times10^{-3}$ K$^{-1}$ for $\lambda_m=3.4$ □m, the expression is satisfied with y=13.3, i.e., approximately 13 half wavelength cavity layers are required to achieve the condition $d\lambda_m/dT|_T=0$.

There is considerable variation in the values of the material properties ($n_H$, $dn_H/dT$, $C_H$, etc.) that appear in for thin films in a multilayer structure and therefore in the predicted value of $d\lambda_m/\lambda_m dT$ or the value of y required to achieve the condition $d\lambda_m/\lambda_m dT=0$. The uncertainty is particularly severe for the value of $dn_H/dT$ for PbTe in view of its magnitude and influence on the value of y. For example, the value of dn/dT for PbTe at $\lambda_m=5$ □m has been reported to be $-1.5\times10^{-3}$ K$^{-1}$ by Zemel, J. N., Jensen, J. D. and Schoolar, R. B., "ELECTRICAL AND OPTICAL PROPERTIES OF EPITAXIAL FILMS OF PBS, PBSE, PB TE AND SNTE", Phys. Rev. 140, A330-A343 (1965), $-2.7\times10^{-3}$ K$^{-1}$ by Piccioli, N., Besson, J. M. and Balkanski, M., "OPTICAL CONSTANTS AND BAND GAP OF PBTE FROM THIN FILM STUDIES BETWEEN 25 AND 300° K", J. Phys. Chem. Solids, 35, 971-977 (1974), and $-2.8\times10^{-3}$ K$^{-1}$ by Weiting, F. and Yixun, Y., "TEMPERATURE EFFECTS ON THE REFRACTIVE INDEX OF LEAD TELLURIDE AND ZINC SELENIDE", Infrared Phys., 30, 371-373 (1990). From the above expression, the corresponding values of y (to the nearest integer) are 9, 17 and 18, respectively.

Figure 3:
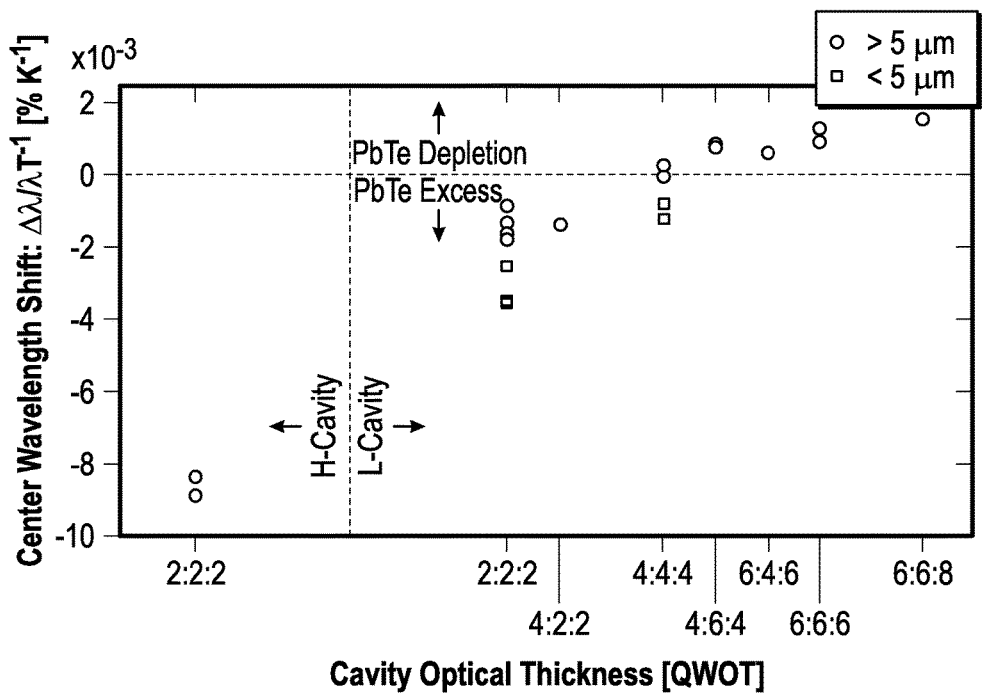
FIG. 3 shows variation of $d\lambda_m/\lambda_m dT$ for a suite of filters fabricated with ZnSe as the low refractive index material and PbTe as the high refractive index material, in accordance with an embodiment of the present disclosure.

In view of the uncertainties in the value of dn/dT for PbTe and therefore the number of low refractive index half wavelength spacers required to achieve $d\lambda_m/dT=0$, a more useful approach is to determine the experimental value of $d\lambda_m/dT$ as a function of the optical thickness of the low refractive index cavities for a suite of filters fabricated by the same method. FIG. 3 shows the variation of $d\lambda_m/\lambda_m dT$ for a suite of filters fabricated with ZnSe as the low refractive index material and PbTe as the high refractive index material. The plot shows that a particular value of $d\lambda_m/\lambda_m dT$ can be achieved by controlling the ratio of low to high refractive index materials in the filter (i.e., a parameter similar to y in the above expression). FIG. 3 shows that for $\lambda_m$<5 µm, the condition $d\lambda_m/\lambda_m dT=0$ is met by a 4:4:4 (i.e., 3 full wavelength or 6 half wavelength cavities (y=6)) filter, while for $\lambda_m$>5 µm a 6:4:6 (y=8) filter is required.

The approach illustrated by FIG. 3 can be used, in accordance with an embodiment of the present disclosure, to fabricate substantially temperature invariant filters over the entire mid-infrared spectral range. In some embodiments of the present disclosure, the substrate may be formed of Si, $SiO_2$, $Al_2O_3$, Ge or ZnSe. In some embodiments of the present disclosure, high refractive index layers can be formed of PbTe, PbSe or PbS, although Ge is also an option. In some embodiments of the present disclosure, the low refractive index layers can be formed of ZnS or ZnSe.

Figure 4A:
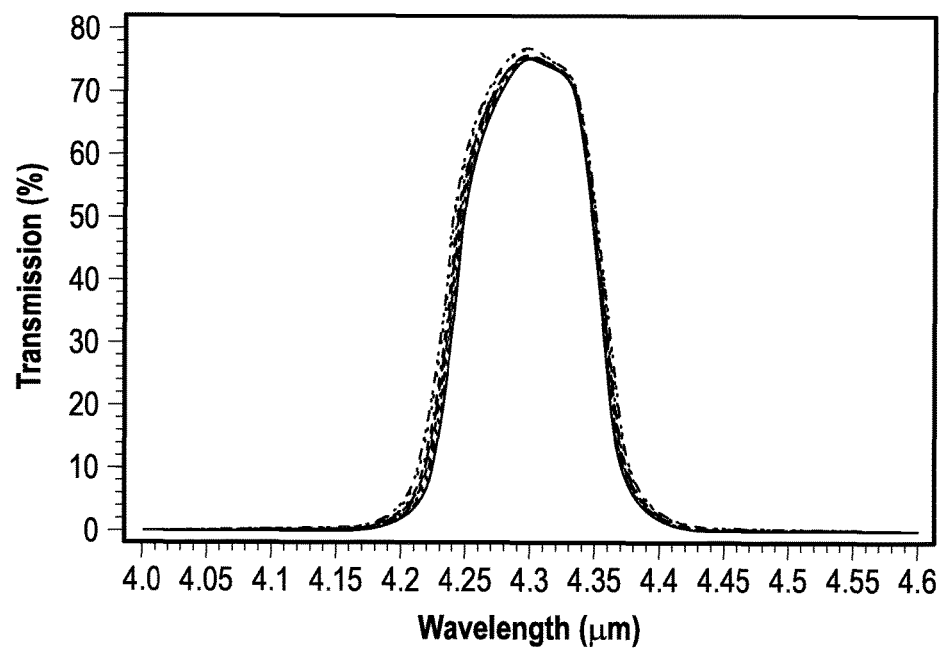
FIG. 4 shows plots of transmissivity against wavelength at a range of temperatures from 25 to 200° C. for (a) a PbTe-based filter having a pass band centred at 4.26 μm, and (b) a PbTe-based filter having a pass band centred at 12.1 μm, in accordance with embodiments of the present disclosure.
Figure 4B:
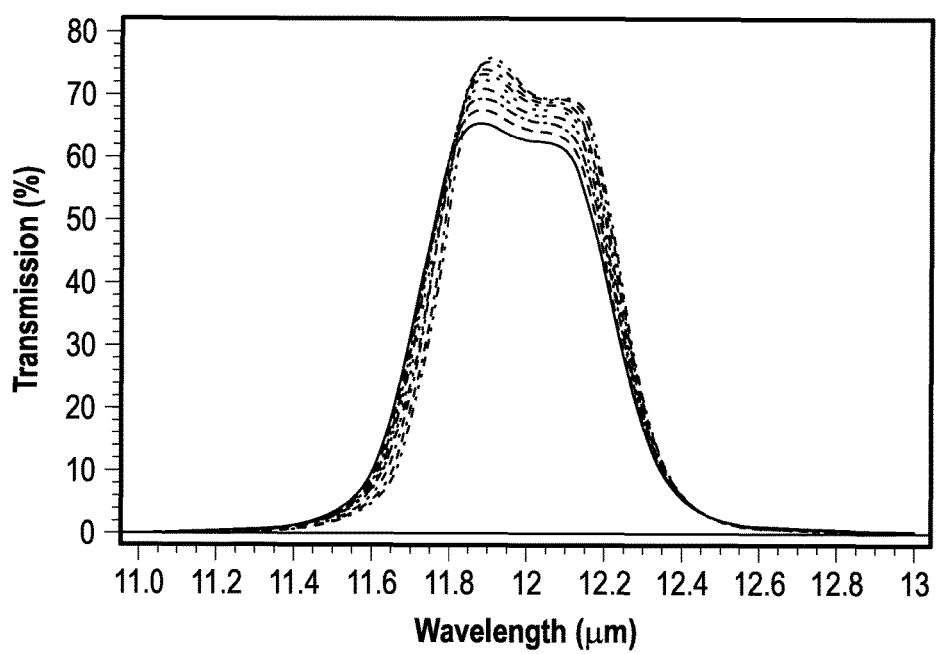

FIG. 4 shows plots of transmissivity against wavelength at a range of temperatures from 25 to 200° C. for (a) a PbTe-based filter having a pass band centred at 4.26 µm with optimum optical matching to the substrate and 3 full wavelength thickness cavities (4:4:4), and (b) a degenerate PbTe-based filter having a pass band centred at 12.1 µm with 3 half wavelength cavities (2:2:2). Similar filters can be produced having pass bands centred at other mid-infrared wavelengths. The value of $d\lambda_m/dT$ for the $\lambda_m$=4.26 µm (4:4:4) filter varies from −0.04 nm/K at 20° C. to +0.03 nm/K at 200° C. and is essentially zero over the temperature range 80-160° C. The value of $d\lambda_m/dT$ for the $\lambda_m$=12.1 µm (2:2:2) filter is −0.21 nm/K, over the temperature range 20-200° C. This allows such filters to deployed downhole, where temperatures can vary from about 25 to 200° C., without the pass band of the filter shifting to such an extent that it no longer corresponds to the absorbance peak of its respective species.

Spectroscopy

Figures 5A, 5B, 5C:
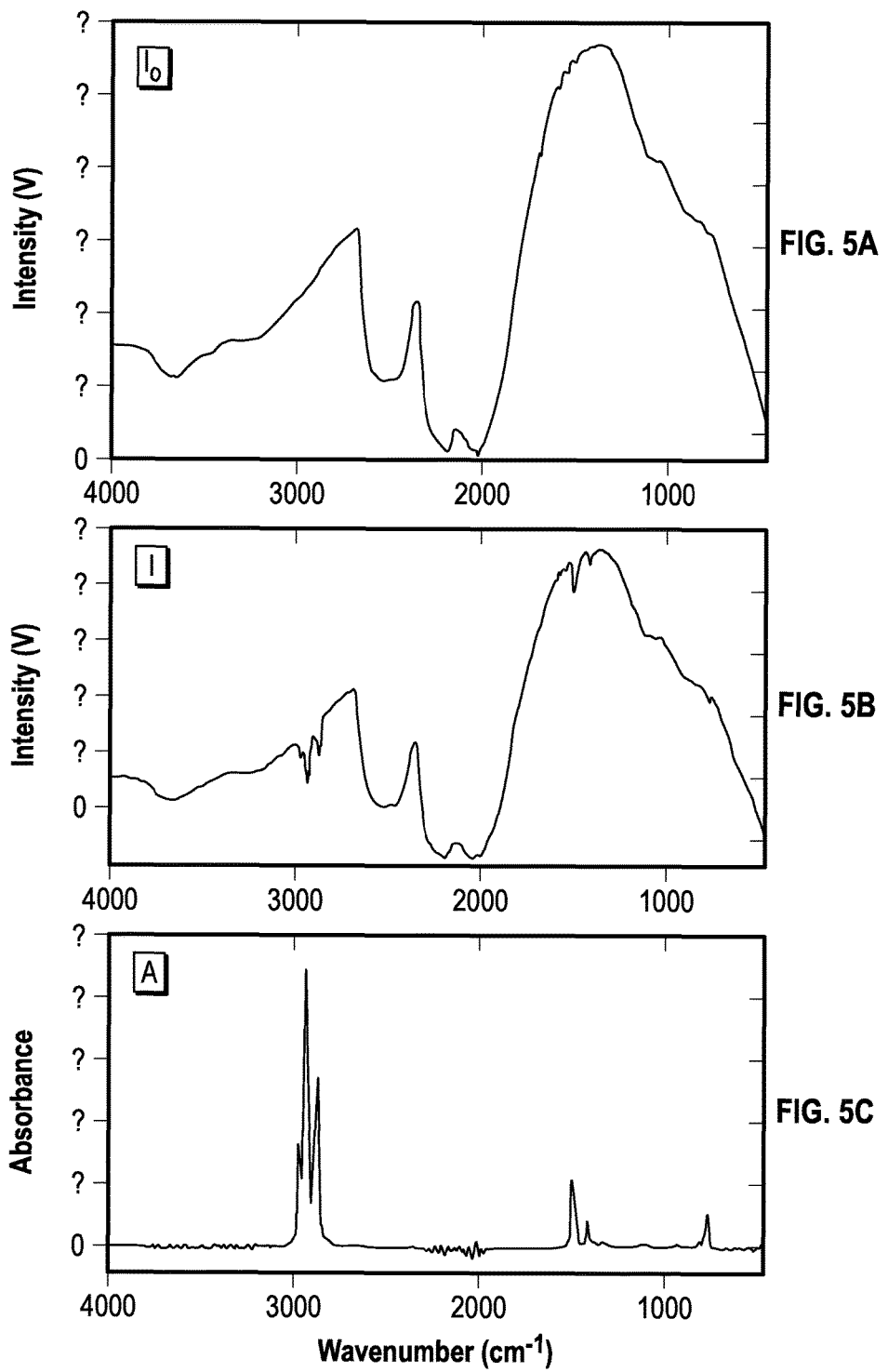
FIG. 5 shows (a) a reference intensity spectrum $I_0$ obtained from a fluid not containing a given species, (b) an intensity spectrum I obtained from the fluid containing the species, and (c) the absorbance spectrum of the species.

The Beer-Lambert law applied to the sensor of FIG. 1 provides that:

$$A=-\log_{10}(I/I_0)$$

where A is the absorbance spectrum by a species in the fluid having an absorbance peak at a wavelengths corresponding to the pass band of the filter 5, I is the intensity spectrum of the infrared radiation detected by the detector 6, and $I_0$ is a reference intensity spectrum. For example, FIG. 5 shows (a) a reference intensity spectrum $I_0$ obtained from a fluid not containing a given species, (b) an intensity spectrum I obtained from the fluid containing the species, and (c) the absorbance spectrum of the species.

Figure 6:
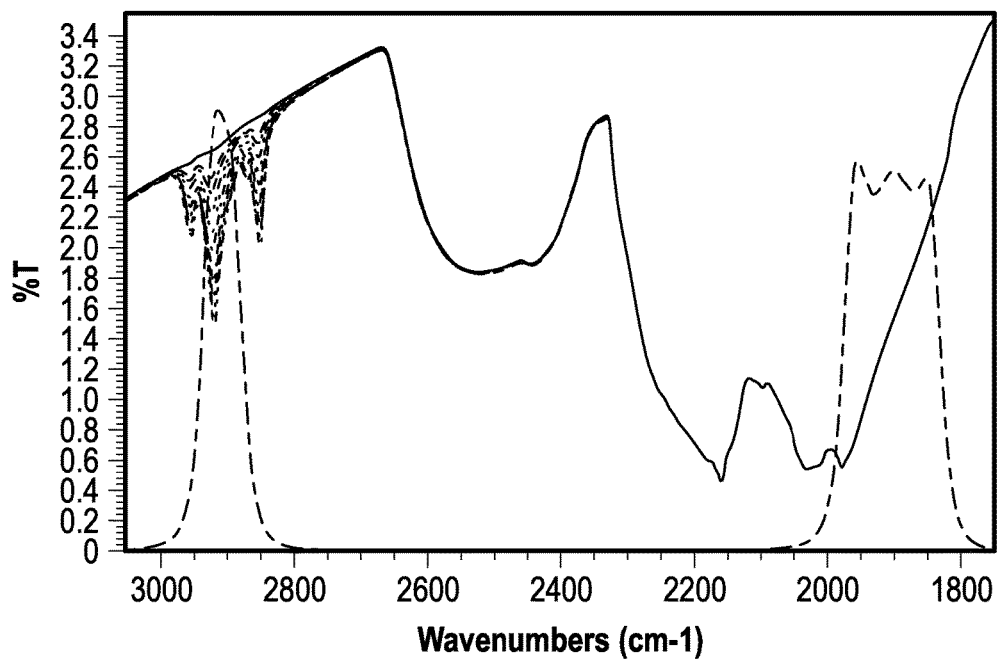
FIG. 6 shows intensity spectra obtained for dodecane dissolved in deuterated chloroform for increasing concentrations of dodecane, the spectra being superimposed with transmissivity plots for a first filter having a pass band of 3000 to 2800 $cm^{-1}$, and a second filter having a pass band of 2000 to 1800 $cm^{-1}$.

FIG. 6 shows intensity spectra obtained for dodecane dissolved in deuterated chloroform for increasing concentrations of dodecane. With increasing hydrocarbon content there is increased absorption in a first wavenumber range of 3000 to 2800 $cm^{-1}$. Conversely, the increasing hydrocarbon content has substantially no effect on absorption in a second wavenumber range of 2000 to 1800 $cm^{-1}$. The second range can thus be used as the reference to the first range. Superimposed on FIG. 6 are transmissivity plots for a first filter having a pass band of 3000 to 2800 $cm^{-1}$, and a second filter having a pass band of 2000 to 1800 $cm^{-1}$. Two spectra are thus, in effect, detected by the filters, the first spectrum being the unfiltered spectrum multiplied by the transmissivity of the first filter and the second sub-spectrum being the unfiltered spectrum multiplied by the transmissivity of the second filter. The pass band areas of the spectra (as determined by the strengths of the signals received by the photodiode detectors), correspond to respective intensity measurements BA and $BA_0$. These are thus used to calculate a modified absorbance A' for dodecane dissolved in deuterated chloroform which is $\ln(BA/BA_0)$.

Figure 7:
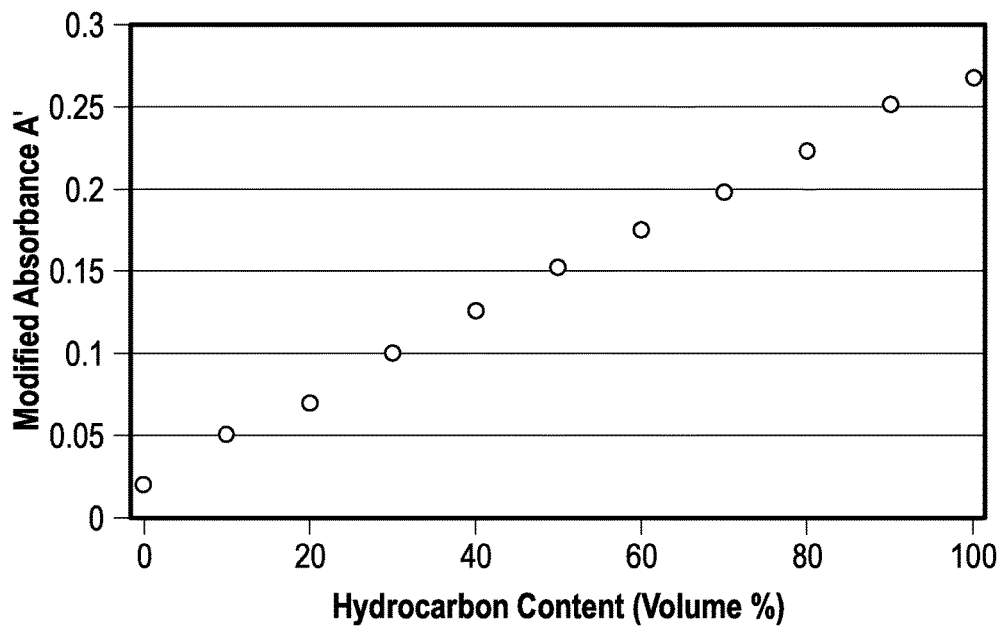
FIG. 7 shows a plot of modified absorbance A' against hydrocarbon content for dodecane dissolved in deuterated chloroform.

FIG. 7 shows a plot of modified absorbance A' against hydrocarbon content for dodecane dissolved in deuterated chloroform. The plot exhibits an approximately linear relationship between A' and hydrocarbon content.

Figure 8:
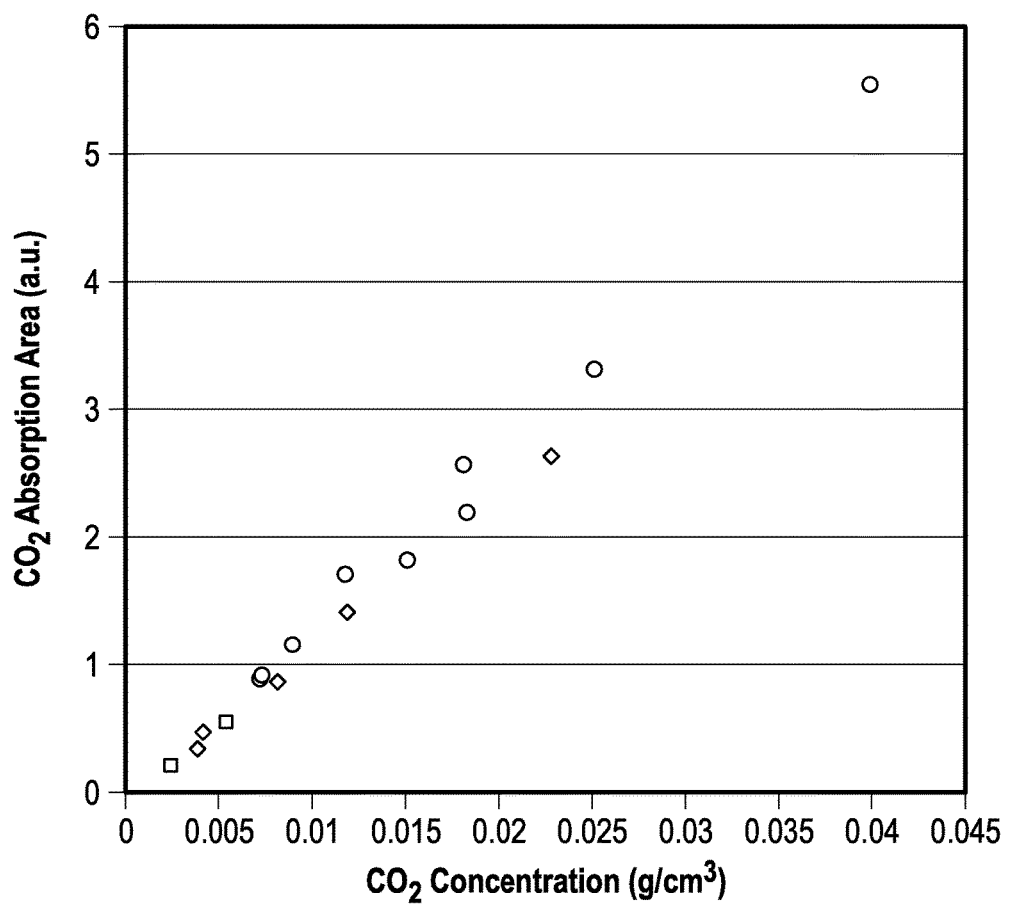
FIG. 8 shows a plot of absorbance against dissolved $CO_2$ concentration in water or hydrocarbon.

Other species can be monitored in this way. For example, FIG. 8 shows a plot of absorbance against dissolved $CO_2$ concentration in water or hydrocarbon under the high partial pressures and temperatures typical of oil field wellbore conditions.

Carbon Dioxide Concentration

The analysis of fluid samples from hydrocarbon wells for the determination of phase behaviour and chemical composition is a critical step in the evaluation of the producibility and economic value of the hydrocarbon reserves. An important factor in determining the economic value of gas and liquid hydrocarbon reserves is their chemical composition, particularly the concentration of gaseous components, such as carbon dioxide. Similarly, the monitoring of fluid composition during production operations can have an important bearing on reservoir management decisions, such as ceasing production from certain zones or applying chemical treatments to producing wells.

A mid-infrared sensor, of the type discussed above, in accordance with an embodiment of the present disclosure, may be used to monitor $CO_2$ concentrations downhole. In particular, in some embodiments of the present disclosure, the sensor may comprise three narrow bandpass filters 5 corresponding to respective absorbance peaks of water, oil and $CO_2$, and a second narrow bandpass filter 5' for a reference portion of the absorbance spectrum. Such an arrangement allows the $CO_2$ concentration to be determined when the window 4 is wetted by a liquid water phase, a liquid oil phase, a mixture of liquid water and liquid oil phases, or when the window is dry.

Figure 9A:
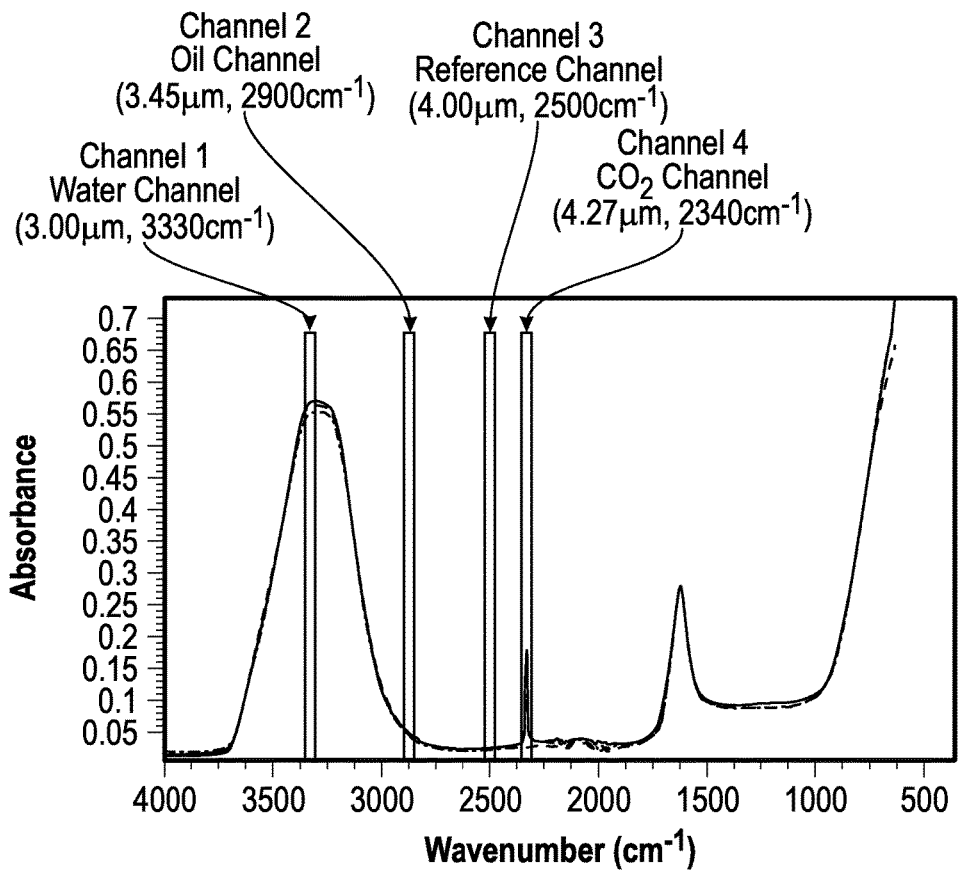
FIG. 9 shows (a) a mid-infrared absorbance spectrum for a water phase and $CO_2$, and (b) a corresponding plot of absorbance against $CO_2$ concentration for $CO_2$ in $H_2O$.
Figure 9B:
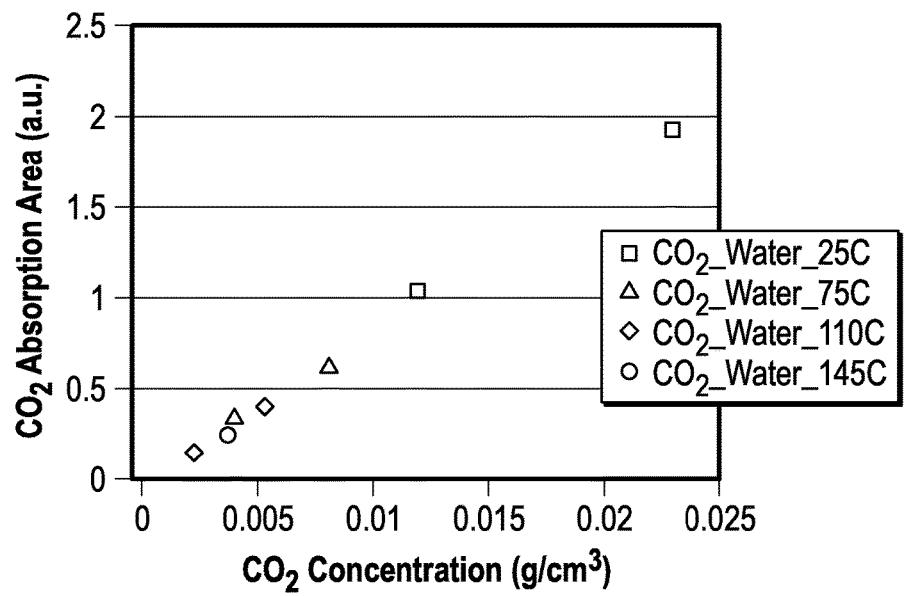

For example, FIG. 9(a) shows an absorbance spectrum for the case where the window 4 is wetted by a water phase. The spectrum is characterised by high absorption by water at 3.00 µm, almost no absorption by oil at 3.45 µm. The $CO_2$ concentration is proportional to the net $CO_2$ absorption, which is the difference between the $CO_2$ channel at 4.27 µm and the reference channel at 4.00 µm. The proportionality constant allowing $CO_2$ concentration in the water phase to be determined from $CO_2$ absorption can be obtained from an experimental plot of $CO_2$ absorbance against dissolved $CO_2$ concentration in water, such as shown in FIG. 9(b).

Figure 10A:
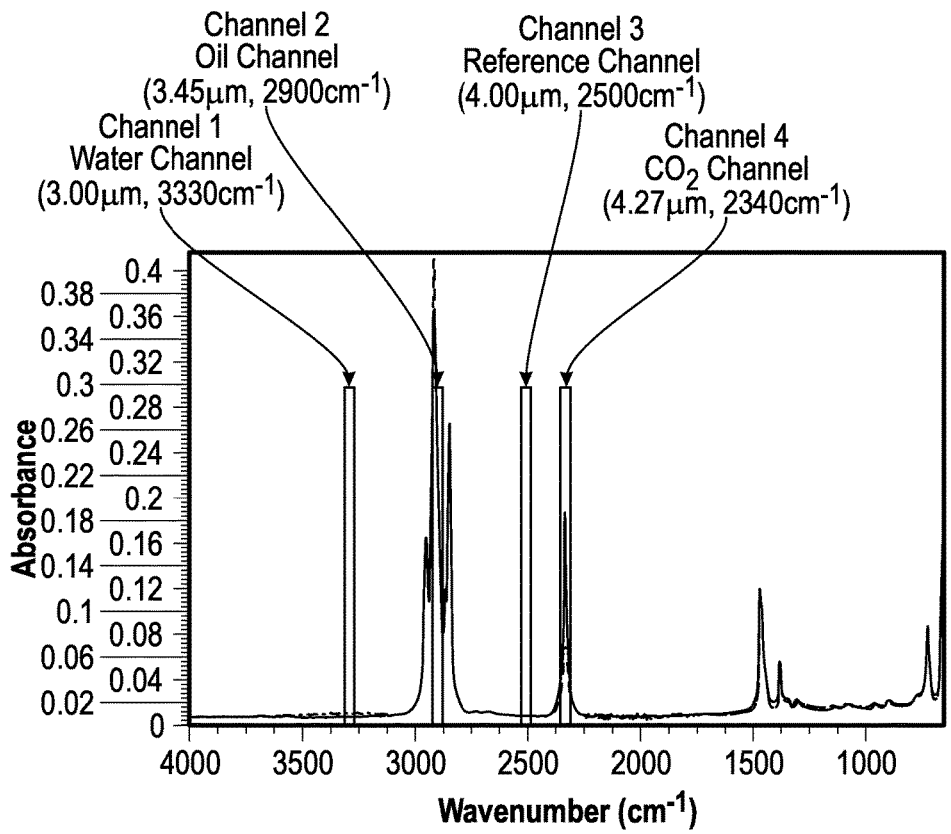
FIG. 10 shows (a) a mid-infrared absorbance spectrum for an oil phase and $CO_2$, and (b) a corresponding plot of absorbance against $CO_2$ concentration for $CO_2$ in oil.
Figure 10B:
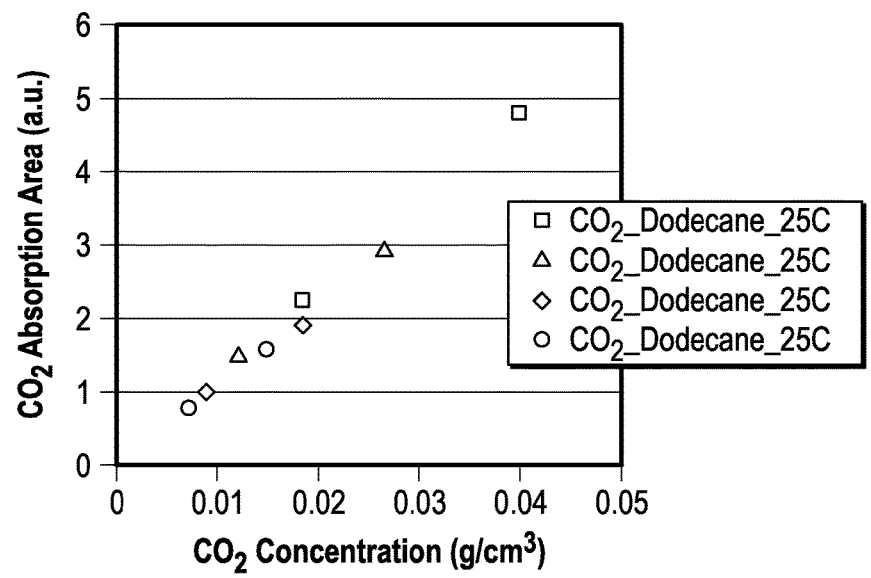

Similarly, FIG. 10(a) shows an absorbance spectrum for the case where the window 4 is wetted by an oil phase. The spectrum is characterised by high absorption by oil at 3.45 um µm almost no absorption by water at 3.00 µm. Again, the $CO_2$ concentration is proportional to the net $CO_2$ absorption, which is the difference between the $CO_2$ channel at 4.27 µm and the reference channel at 4.00 µm. The proportionality constant allowing $CO_2$ concentration in the oil phase to be determined from $CO_2$ absorption can be obtained from an experimental plot of $CO_2$ absorbance against dissolved $CO_2$ concentration in oil, such as shown in FIG. 10(b).

Figure 11:
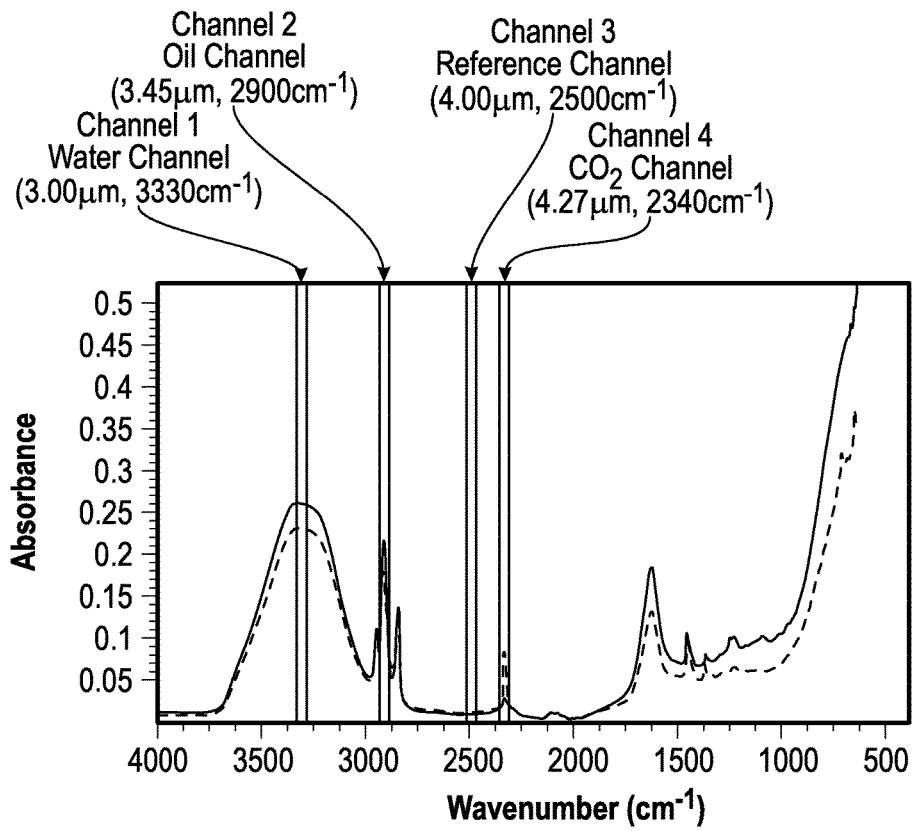
FIG. 11 shows a mid-infrared absorbance spectrum for a water phase, an oil phase and $CO_2$.

Next, FIG. 11 shows an absorbance spectrum for the case where the window 4 is wetted by a mixture of water and oil phases. The spectrum is characterised by absorption by water at 3.00 µm and by oil at 3.45 µm. Again the $CO_2$ concentration is proportional to the net $CO_2$ absorption, which is the difference between the $CO_2$ channel at 4.27 µm and the reference channel at 4.00 µm. However, the proportionality constant is slightly different for water and for oil because their refractive indices, and thus their depths of investigation, are different. Specifically, oil has higher refractive index than water, thus its depth of investigation is deeper and potentially more $CO_2$ is sensed by the sensor in oil than in water. Thus, when the window is wetted by a mixture of both water and oil phase, the mixture proportionality constant is between those of water and oil, but can be calculated from therefrom. For example, In some embodiments of the present disclosure, a "lever rule" may be used, whereby if the water peak height is X % of its full height and the oil peak height is (100−X) % of its full height, the mixture proportionality constant is the sum of X % of the water proportionality constant and (100−X) % of the oil proportionality constant. More elaborate schemes can be used, in other embodiments, but the simple "lever rule" approach works reasonably well because the difference between the water and oil proportionality constants is in any event not great.

Figure 12:
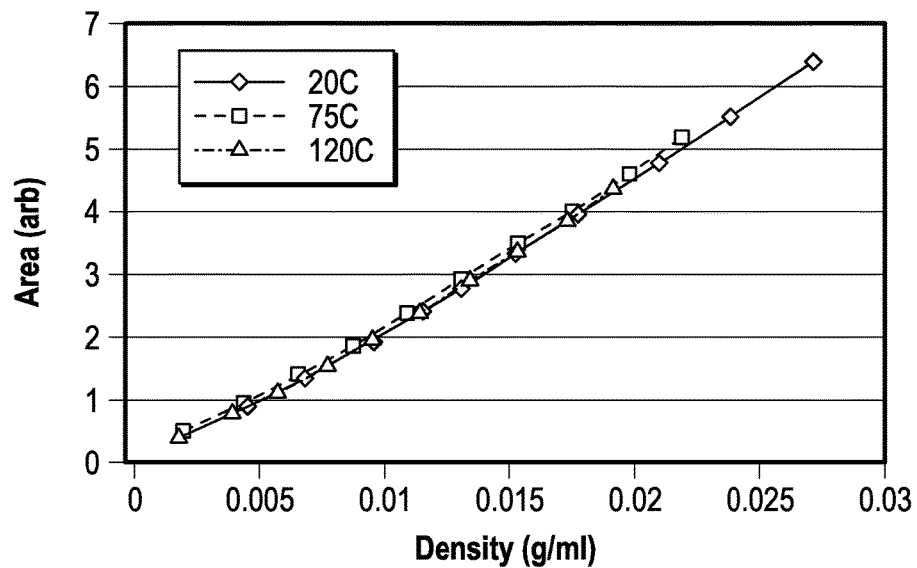
FIG. 12 shows a plot of absorbance against $CO_2$ concentration for $CO_2$ in gas phase.

Under some circumstances, the sensor window 5 may be dry. The spectrum is characterised by almost no absorption by water at 3.00 μm or by oil at 3.45 μm. $CO_2$ concentration is proportional to the net $CO_2$ absorption, which is the difference between the $CO_2$ channel at 4.27 μm and the reference channel at 4.00 μm. The proportionality constant allowing $CO_2$ concentration in the gas phase to be determined from $CO_2$ absorption can, in accordance with an embodiment of the present disclosure, be obtained from an experimental plot of $CO_2$ absorbance against $CO_2$ concentration in gas phase, such as shown in FIG. 12.

Monitoring of $CO_2$ concentration can be particularly useful when performed in combination with monitoring of mineral acid concentrations. In particular, a mineral acid sensor can provide a measure of how much acid is being deployed to stimulate a carbonate formation, and the $CO_2$ sensor, by measuring the amount of $CO_2$ produced, can provide a measure of the effectiveness of that acid deployment.

Heater

As mentioned above, the sensor of FIG. 1 may, in some embodiments of the present disclosure, comprise a heater 8 that is operable to locally heat the window 4, thereby cleaning the surface of the window in contact with the fluid.

Cleaning the window in this manner may be particularly effective, compared to other techniques such as ultrasonic cleaning or mechanical wiper cleaning.

The window 4 can be formed, for example, in some embodiments of the present disclosure, of diamond (e.g. by chemical vapour deposition). A central (typically undoped) area of the window may be mid-infrared transmissive, while an annular encircling area of the window may be made semiconductive, e.g. by boron doping that part of the window. The heater 8 can then be a simple electrical power source which sends a current through the window to induce resistive heating of the encircling area. The central area of the window is then heated by thermal conduction from the encircling area. Boron-doping of diamond components is discussed in U.S. Pat. No. 7,407,566.

In some embodiments of the present disclosure, the heater 8 may be able to heat the window to at least 400° C. This is higher than the 374° C. super-critical point for water, where super-critical water comprises a good cleaner and oxidiser. In some embodiments of the present disclosure, it is unnecessary to keep the window at high temperature for a long time period. In particular, less than a microsecond at peak temperature may be enough for cleaning purposes, with longer periods requiring more power and increasing the risk of overheating of other parts of the sensor.

Pressure Pulse Cleaner

In addition, or as an alternative, to the above heater, cleaning of the window 4 may, in some embodiments of the present disclosure, be performed by providing the sensor with a pressure pulse arrangement. For example, the sensor may be located on a fluid flow line between a pump for the fluid and an exit port from the flow line. With the exit port in a closed position, the fluid pressure can be increased in front of the window to above hydrostatic pressure by the pump. Subsequent of opening the exit port creates a sudden pressure difference that flushes the flowline fluid, e.g. to the borehole. The sudden movement of dense fluid in front of the window dislodges and carries away window contamination. A 1000 psi (6.9 MPa) pressure pulse is generally sufficient in most cases.

All references referred to above are hereby incorporated by reference.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions and alterations herein without departing from such scope.

The invention claimed is:

1. A sensor for monitoring $CO_2$ in a fluid, the sensor comprising:
    an internal reflection window configured in use to contact the fluid;
    a mid-infrared light source configured to direct a beam of mid-infrared radiation into the window to provide for attenuated internal reflection of the beam of mid-infrared radiation at an interface between the window and the fluid;
    a set of three narrow bandpass filters configured to filter the internally reflected mid-infrared radiation received from the window wherein:
        a first narrow bandpass filter of the set of three narrow bandpass filters comprises a water filter and is configured to preferentially transmit mid-infrared radiation over a band of wavelengths corresponding to respective absorbance peaks of water;
        a second narrow bandpass filter of the set of three narrow bandpass filters comprises an oil filter and is configured to preferentially transmit mid-infrared radiation over a band of wavelengths corresponding to respective absorbance peaks of oil; and
        a third narrow bandpass filter of the set of three narrow bandpass filters comprises a $CO_2$ filter and is configured to preferentially transmit mid-infrared radiation over a band of wavelengths corresponding to respective absorbance peaks of $CO_2$;
    one or more infrared detector(s) configured to detect filtered mid-infrared radiation transmitted through the set of three narrow bandpass filters; and
    a processor arrangement, operably coupled to the one or more infrared detector(s) and configured to measure intensities of the detected mid-infrared radiation transmitted through the set of three narrow bandpass filters and determine therefrom an amount of $CO_2$ in the fluid, notwithstanding whether the fluid contacting the window is a liquid water-based phase, a liquid oil-based phase, a mixture of liquid water- and liquid oil-based phases, or a gas phase, wherein the sensor further comprises at least one of:
a heater configured to heat the window and clean a surface of the window in contact with the fluid; or
a pressure pulse arrangement configured to produce a pressure pulse in the fluid at the window and clean the surface of the window in contact with the fluid.

2. The sensor according to claim 1, wherein the first, second, and third narrow bandpass filters of the set of three narrow bandpass filters preferentially transmit mid-infrared radiation over bands of wavelengths corresponding to absorbance peaks of about 3330 $cm^{-1}$ for water, about 2900 $cm^{-1}$ for oil, and about 2340 $cm^{-1}$ for $CO_2$.

3. The sensor according to claim 1, wherein, to determine the amount of $CO_2$ in the fluid, the processor arrangement calculates the phase of the fluid from the measured intensities of the mid-infrared radiation transmitted through the water and oil filters, and then calculates from the phase of the fluid and the measured intensity of the mid-infrared radiation transmitted through the $CO_2$ filter the amount of $CO_2$ in the fluid.

4. The sensor according to claim 3, wherein the processor arrangement uses the refractive index of the fluid, derived from the phase of the fluid, in the calculation of the amount of $CO_2$ in the fluid.

5. The sensor according to claim 1, wherein each narrow bandpass filter of the set of three narrow bandpass filters is configured such that its wavelength transmission band is substantially temperature invariant over all temperatures in the range from about 25° C. to about 150° C.

6. The sensor according to claim 5, wherein each of the narrow bandpass filters comprises an interference filter having a substrate and at each opposing side of the substrate alternating high and low refractive index layers.

7. The sensor according to claim 1, further comprising:
a reference narrow bandpass filter configured to transmit mid-infrared radiation over a band of wavelengths corresponding to a reference portion of the absorbance spectrum of the fluid, wherein the or a further infrared detector is configured to detect filtered mid-infrared radiation transmitted through the reference filter, and wherein the processor arrangement is configured to measure a reference intensity of the detected mid-infrared radiation transmitted through the reference filter and use the measured reference intensity in the determination of the amount of the $CO_2$ in the fluid.

8. The sensor according to claim 1, wherein the beam of mid-infrared radiation is pulsed.

9. The sensor according to claim 1, wherein the window comprises one of a diamond window or a sapphire window.

10. A method of monitoring $CO_2$ in a fluid, the method comprising:
providing the sensor of claim 1 such that the internal reflection window is in direct contact with the fluid; and
operating the sensor to determine an amount of $CO_2$ in the fluid.

11. A well tool including the sensor of claim 1.

12. A method of determining an amount of $CO_2$ in a fluid, the method comprising:
receiving respective measured intensities of mid-infrared radiation filtered by three narrow bandpass filters which preferentially transmit mid-infrared radiation over bands of wavelengths corresponding to respective absorbance peaks of water, oil, and $CO_2$, the mid-infrared radiation, prior to filtering, being produced by directing a beam of mid-infrared radiation into an internal reflection window for attenuated internal reflection at an interface between the window and a fluid in direct contact with window;
calculating from the measured intensities of the mid-infrared radiation filtered by the water and oil filters the phase of the fluid;
calculating from the phase of the fluid and the measured intensity of the mid-infrared radiation filtered by the $CO_2$ filter the amount of $CO_2$ in the fluid; and
cleaning a surface of the window in contact with the fluid using at least one of a heater configured to heat the window or a pressure pulse arrangement configured to produce a pressure pulse in the fluid at the window.

13. A method for detecting or measuring $CO_2$ in a fluid, the method comprising:
directing a beam of mid-infrared radiation into a window in contact with the fluid;
passing an attenuated internal reflection of the beam of mid-infrared radiation at an interface between the window and the fluid through a set of three narrow bandpass filters configured to filter the internally reflected mid-infrared radiation received from the window wherein:
a first narrow bandpass filter of the set of three narrow bandpass filters comprises a water filter and is configured to preferentially transmit mid-infrared radiation over a band of wavelengths corresponding to respective absorbance peaks of water;
a second narrow bandpass filter of the set of three narrow bandpass filters comprises an oil filter and is configured to preferentially transmit mid-infrared radiation over a band of wavelengths corresponding to respective absorbance peaks of oil; and
a third narrow bandpass filter of the set of three narrow bandpass filters comprises a $CO_2$ filter and is configured to preferentially transmit mid-infrared radiation over a band of wavelengths corresponding to respective absorbance peaks of $CO_2$;
using one or more infrared detector(s) to detect the mid-infrared radiation passing through each of the set of three narrow bandpass filters;
measuring intensities of the detected mid-infrared radiation passed through the set of three narrow bandpass filters;
determining an amount of $CO_2$ in the fluid from the measured intensities, wherein the fluid contacting the window is one or more of a liquid water-based phase, a liquid oil-based phase, a mixture of liquid water and liquid oil-based phases, or a gas phase; and
cleaning a surface of the window in contact with the fluid using at lesat one of a heater configured to heat the window or a pressure pulse arrangement configured to produce a pressure pulse in the fluid at the window.

14. The method of claim 13, wherein determining the amount of $CO_2$ in the fluid from the measured intensities comprises determining the phase of the fluid from the measured intensities of the mid-infrared radiation transmitted through the water and oil filters and calculating from the phase of the fluid and the measured intensity of the mid-infrared radiation transmitted through the $CO_2$ filter the amount of $CO_2$ in the fluid.

15. The method of claim 14, wherein a refractive index of the fluid that is derived from the phase of the fluid is used to determine the amount of $CO_2$ in the fluid.

16. The method of claim 13, wherein each narrow bandpass filter of the set of three narrow bandpass filters is configured such that its wavelength transmission band is substantially temperature invariant over all temperatures in the range from about 25° C. to about 150° C.

17. The method of claim 13, further comprising:
passing the attenuated internal reflection of the beam of mid-infrared radiation through a reference narrow bandpass filter configured to transmit mid-infrared radiation over a band of wavelengths corresponding to a reference portion of the absorbance spectrum of the fluid;
measuring an intensity of the reflected mid-infrared radiation transmitted through the reference filter; and
using the measured reference intensity in the determination of the amount of the $CO_2$ in the fluid.

18. The method of claim 13, wherein the beam of mid-infrared radiation is pulsed.

* * * * *